United States Patent [19]

Weier

[11] Patent Number: 5,558,231

[45] Date of Patent: Sep. 24, 1996

[54] AUTOMATIC SORTING MACHINE FOR SORTING AND CLASSIFYING SMALL PRODUCTS OF THE PHARMACEUTICAL AND CONFECTIONERY INDUSTRIES ACCORDING TO FORM AND COLOR

[75] Inventor: Detlef Weier, Heiligenberg, Germany

[73] Assignee: Maschimpex GmbH, Friedrichshafen, Germany

[21] Appl. No.: 440,974

[22] Filed: May 15, 1995

[30] Foreign Application Priority Data

May 14, 1994 [DE] Germany ............ 44 17 015.7

[51] Int. Cl.⁶ .................................. B07C 5/342
[52] U.S. Cl. ............................ 209/580; 209/939
[58] Field of Search .................. 209/580, 581, 209/538, 587, 920, 939; 356/402

[56] References Cited

U.S. PATENT DOCUMENTS

| | | |
|---|---|---|
| 2,843,253 | 7/1958 | Peterson et al. . |
| 3,901,381 | 8/1975 | Quinn . |
| 3,938,653 | 2/1986 | Senger . |
| 5,190,137 | 3/1993 | Tas . |

FOREIGN PATENT DOCUMENTS

| | | |
|---|---|---|
| 0172663 | 2/1986 | European Pat. Off. . |
| 0496262 | 7/1992 | European Pat. Off. . |
| 2709787 | 9/1978 | Germany . |
| 3608398 | 10/1986 | Germany . |
| 3724240 | 2/1989 | Germany . |
| 8814491 | 6/1989 | Germany . |
| 3842098 | 6/1989 | Germany . |
| 3908862 | 9/1989 | Germany . |
| 3943371 | 7/1990 | Germany . |
| 9116289 | 9/1992 | Germany . |
| 4124278 | 1/1993 | Germany . |
| 4221107 | 1/1994 | Germany . |
| 2267474 | 12/1993 | United Kingdom . |

OTHER PUBLICATIONS

"Optical Sorter Boosts Limestone–Mine Profits in Finland", by M. H. Tulloch, in Photonics Spectra, Aug. 1993, p. 20.
"Technik, die sehen kahn", by C. Thony, in Technische Rundschau, Mar. 1990, pp. 14–17.

Primary Examiner—D. Glenn Dayoan
Attorney, Agent, or Firm—Greenblum & Bernstein P.L.C.

[57] ABSTRACT

Automatic sorting machine for sorting and classifying small products of the pharmaceutical and confectionery industries according to form and color. The present invention pertains to an automatic sorting machine for sorting and classifying these products for deviations, via optoelectronic specimen recognition, with the machine including a vibratory inlet device in which the products to be sorted are separated in order to present same to a delivery device for conveying the separated products through a beam/light path of a camera. Each product is optically comprehended by the camera and encoded into electrical signals, via which specimen recognition is carried out through appropriate electronics in order to eliminate unrecognized products having improper deviations. In order to classify the product with substantially higher processing speeds and in order to achieve a defined color report, a color-line camera is provided, which pans the beam/light path of the camera in the feeding direction of the product over a determined conveying track, and the product, during its throughput through the panned beam/light path, is rotated about an axis parallel with the scanning line.

23 Claims, 7 Drawing Sheets

AUTOMATIC SORTING MACHINE FOR SORTING AND CLASSIFYING SMALL PRODUCTS OF THE PHARMACEUTICAL AND CONFECTIONERY INDUSTRIES ACCORDING TO FORM AND COLOR

CROSS REFERENCE TO RELATED APPLICATIONS

This application claims the priority of German Application No. P 44 17 015.7, filed May 14, 1994, the disclosure of which is incorporated herein by reference in its entirety.

BACKGROUND OF THE INVENTION

1. Field of the Invention

This invention pertains to an automatic sorting machine for sorting and classifying small products, by means of optoelectronic specimen recognition, the machine comprising a vibratory inlet device wherein the products to be sorted are separated; a camera having a beam/light path; a delivery device for conveying the separated products, through the beam/light path; the camera being utilized for optically comprehending each product and for obtaining electronic signals; and means for evaluating the electronic signals for specimen recognition for deviations of the product, for producing an elimination signal, for eliminating defective products and unrecognized products.

2. Discussion of the Background of the Invention and Material Information

Such automatic sorting machines have become known in a myriad of embodiments and generally utilize so-called optoelectronic specimen recognition of the product. Such automatic sorting machines are utilized in the pharmaceutical and confectionery industries in order to make a good/bad determination or report of manufactured products. It is known to arrange these products in a vibratory feeder and feed same, via a delivery device, to an optical recognition device.

It is also known to construct the feeding device as a conveyor and to convey the products through the beam/light path of a CCD-camera. The camera comprehends the offered product and, from the signal of the CCD-matrix, a specimen recognition is accomplished in the manner that unacceptable form and color embodiments of the product cause the formation of an elimination signal which so controls the conveying apparatus that the recognized and classified product is selectively, depending upon the result of the classification, conveyed to differing elimination or exit tracks where acceptable products are separated from unacceptable products.

These known automatic sorting machines have the disadvantage of having but a relatively slow working speed or velocity since the analysis or evaluation of the picture, recognized by the camera with the aid of electronic specimen recognition programs, involves substantial difficulties which in turn cause relatively long processing times. It is known to examine the products with a plurality of cameras from all sides thereof, whereby the cameras are fixed and the products are not rotated. This however has the disadvantage that the cameras also encompass the transition regions of the product which in turn are superimposed with light reflexes and light colors, so that the evaluation in these regions is not optimized.

Up to now it was not known to faultlessly recognize color, geometry, differing surface characteristics and deviations of desired predetermined properties.

The task or object of this invention is therefore to further develop automatic sorting machines of the previously described type so that, at a substantially greater processing speed, the shape of the product can be recognized from all sides thereof; can be classified; and that a definite color determination can be made.

SUMMARY OF THE INVENTION

The solution of the stated task or object of the invention is set forth in the appended claims. Specifically, this task or object is achieved ny an automatic sorting machine for sorting and classifying small products, by means of optoelectronic specimen recognition, the machine comprising a vibratory inlet device wherein the products to be sorted are separated; a camera having a beam/light path; a delivery device for conveying the separated products, through the beam/light path; the camera being utilized for optically comprehending each product and for obtaining electronic signals; means for evaluating the electronic signals for specimen recognition for deviations of the product, for producing an elimination signal, for eliminating defective products and unrecognized products, wherein the camera is a color-line camera, whose beam/light path is so movably arranged that a beam/light path thereof, in a feeding direction of the product, pans the beam/light path over a predetermined conveying track, wherein the product, during the throughput thereof through the panned beam/light path, is rotated about an axis parallel to a scanning line.

In a variation of the automatic sorting machine of this invention, at least one of the camera and a reorientation mirror synchronously pan the feeding movement of the product.

In a further variation of the automatic sorting machine of this invention, at least one of the camera and a reorientation mirror is moved synchronously with the product over a predetermined distance.

In another variation of the automatic sorting machine of this invention, the reorientation mirror is a transverse mirror turnable about a central longitudinal axis.

In still a further variation of the automatic sorting machine of this invention, the reorientation mirror is a polygonal mirror turnable about a longitudinal axis.

In still another variation of the automatic sorting machine of this invention, several products are transportable parallel to each other in several adjacent paths, through the beam/light path of the camera. Preferably, several cameras are adjacently arranged, whereby each camera always surveys several paths of the products.

In yet another variation of the automatic sorting machine of this invention, the delivery device is comprised of a turning station and a roller track, the roller track having rollers arranged perpendicularly to the feeding direction. Preferably, the rollers are rotatable about their respective longitudinal axes.

An additional variation of the automatic sorting machine of this invention further includes a multi track delivery of the products on correspondingly arranged tracks of the roller track.

In a further variation of the automatic sorting machine of this invention, lateral boundaries are provided for each track.

In another variation of the automatic sorting machine of this invention, fixed strips are attached above the roller track.

A yet further variation of the automatic sorting machine of this invention includes a lower illumination device attached underneath the roller track, the illuminating device facing a color filter in order to spotlight the product, from below, between the rollers.

A still further variation of the automatic sorting machine of this invention includes an attached upper illumination device, having illuminating bodies, whose beam/light paths are thusly reflected that a diffused white brightening light is produced on the products.

An important feature of this invention is that the optical specimen recognition is accomplished with a color-line camera in whose beam/light path at least one movable mirror is arranged, with the mirror panning the beam/light path of the camera in the feeding direction of the product.

Another embodiment of the invention utilizes a movable camera, instead of a movable mirror, wherein the camera is moved (transversely) synchronously in the transporting direction of the product over a predetermined distance. The sorting is accomplished here by means of differing criteria such as color, geometry, surface characteristics, by means of one or more imprints on the product, black-white contrasts, surface form, soiling, errors or damage to the product. The product can be sorted per one or more of the noted criteria. The degree or weight of error can be adjusted hereby. Thus, a desired or nominal value, having a defined tolerance band or region can be set forth within which the one or several measured criteria must fall. Herewith, the desired/nominal values and the tolerance band/region can be adjusted.

Thus, for example, a foreign product, a crack or a wrong imprint, a dent or the soiling of an otherwise satisfactory or acceptable product can be determined. In addition, coating errors, color errors and other deviations can also be recognized.

A further important feature of the invention thus is the utilization of a color-line camera, which has the advantage that only a line-shaped scanning of the product takes place, thus requiring the comprehension of substantially less picture data in comparison with a matrix-type camera. In this manner, the entire electronic specimen or sample recognition can proceed much more rapidly, since only a fraction of the data to be processed is required in comparison with a matrix-type camera.

The use of a matrix-type camera would result in the acquisition of additional multiplicities of data in comparison with the inventive use of a color-line camera.

A further major feature of this invention is that the product, during the throughput thereof, in the feeding direction, while being panned by the beam/light path, is simultaneously being turned or rotated about its longitudinal axis, which essentially dictates or presupposes the use of rotationally symmetrical products.

Therewith it is now possible, for the first time, that the product, in the region of its entire generated surface, can be observed and evaluated with a single color-line camera without requiring expensive further arrangements. A substantial characteristic or feature of this invention is the turning or rotation of the product about its longitudinal axis through the beam/light path of the color-line camera.

The advantage that is associated therewith is that the product is spotlighted or impinged by light sources only on its sides and that the camera can observe the product practically perpendicularly and at an angle relative to the light sources. This provides the advantage that interfering light reflexes no longer detract from the camera picture, since the camera investigates but a quite small surface area of the product when the light reflexes do not interfere.

That, according to the invention, the product is rotated and that the camera, with reference to this rotation, is fixed, provides an additional advantage, namely that any rotational anomalies of the product are easily determined by the camera. This, for example, is not possible with fixed cameras, which view a fixed product from all sides.

The transporting of the product between defined arrays of a movable roller track or conveyor provides the advantage that the product is conveyed geometrically correct and without misalignment and thus it is not necessary to correct the measured data for misalignment during the picture analysis in the cameras. An additional advantage is that, due to the lack of misalignment during the conveying, no interfering light reflexes occur which normally must be accepted in current state of the art arrangements of this type which involve misaligned products.

During the picture data processing of dual-color products (for example, capsules with differing color caps or tablets) the advantage arises that, as per the present invention, the product is rotated during camera surveillance and that thus any deviation (for example a biased cap, distorted capsule body, etc.) is easily recognized by surveying the color-deviating area boundary of the capsule.

The third major feature or characteristic of this invention is, that the beam-light path of the color-line camera pans the product and is so synchronized that the camera views a substantially non-moving product, the latter being turned about its longitudinal axis during its throughput through the panning light path.

The utilization of such a mirror permits the use of several preferred embodiments thereof.

In a first embodiment of this invention, it is preferred that a transverse mirror is utilized which is turned about its longitudinal axis. The use of such a transverse mirror entails the advantage that its turning or rotation can be relatively readily synchronized with the feeding movement of the roller track or conveyor, thus permitting high processing speed.

In a second embodiment of this invention, the transverse mirror is replaced with a swingable or pivotable polygonal mirror, that is pivotable about its central longitudinal axis.

In a third embodiment of this invention, the mirror is arranged in a linearly adjustable manner. It is also possible to alternatively or additionally mount the camera in a movable manner.

Thus, the product receives a translatory movement as a result of its conveyance on a roller track or conveyor and an additional rotational movement via the rotation of the product about its longitudinal axis, with the superimposed movements being recognized by the color-line camera.

Herewith it is preferred, that not only one product is transported through the beam/light path of the camera, but that several products, parallel to each other, on several tracks of the roller track, are transported through the beam/light path of the camera. In this manner, the processing speed of the automatic sorting machine of this invention is multiplied, since in a single sorting operation, for example, 1 to 10 tracks can be simultaneously sorted.

It should be evident that a duplication of the roller track is possible, wherein an additional camera is associated with each roller track, so that not only a single camera measures or observes a multi-path roller track, but that each camera is associated with a multi-path roller track.

Generally, two different cameras are utilized wherein each camera is associated with, for example, six tracks, so that hereby a very high processing speed is achieved.

Due to the controlled passing by or through of the product through the beam/light path of the associated camera, it is now possible, for the first time, to recognize the surface of the product at high resolution and to evaluate same. For example, herewith faulty products of the product capsule, ghost or double prints, various deformations of the product capsule (even end wall deformations) shape or form deviations, color deviations, size deviation and the like, can be satisfactorily observed even at high processing speeds. In addition, destructions of the surface structure can also be recognized.

The task or object of the present invention is set forth not only in the subject matter of the individual patent claims but also in the combination of the individual patent claims with each other. All of the disclosed data and properties within the confines of this application, particularly the actual embodiments set forth in the drawings, are deemed to disclose patentable subject matter.

BRIEF DESCRIPTION OF THE DRAWINGS

The invention will be better understood and objects other than those set forth above will become apparent when consideration is given to the following detailed description thereof. Such description makes reference to the annexed drawings wherein throughout the various figures of the drawings, there have generally been used the same reference characters to denote the same or analogous components and wherein.

DETAILED DESCRIPTION OF THE PREFERRED EMBODIMENTS

With respect to the drawings it is to be understood that only enough of the construction of the invention and the surrounding environment in which the invention is employed have been depicted therein, in order to simplify the illustrations, as needed for those skilled in the art to readily understand the underlying principles and concepts of the invention.

Figure 1:
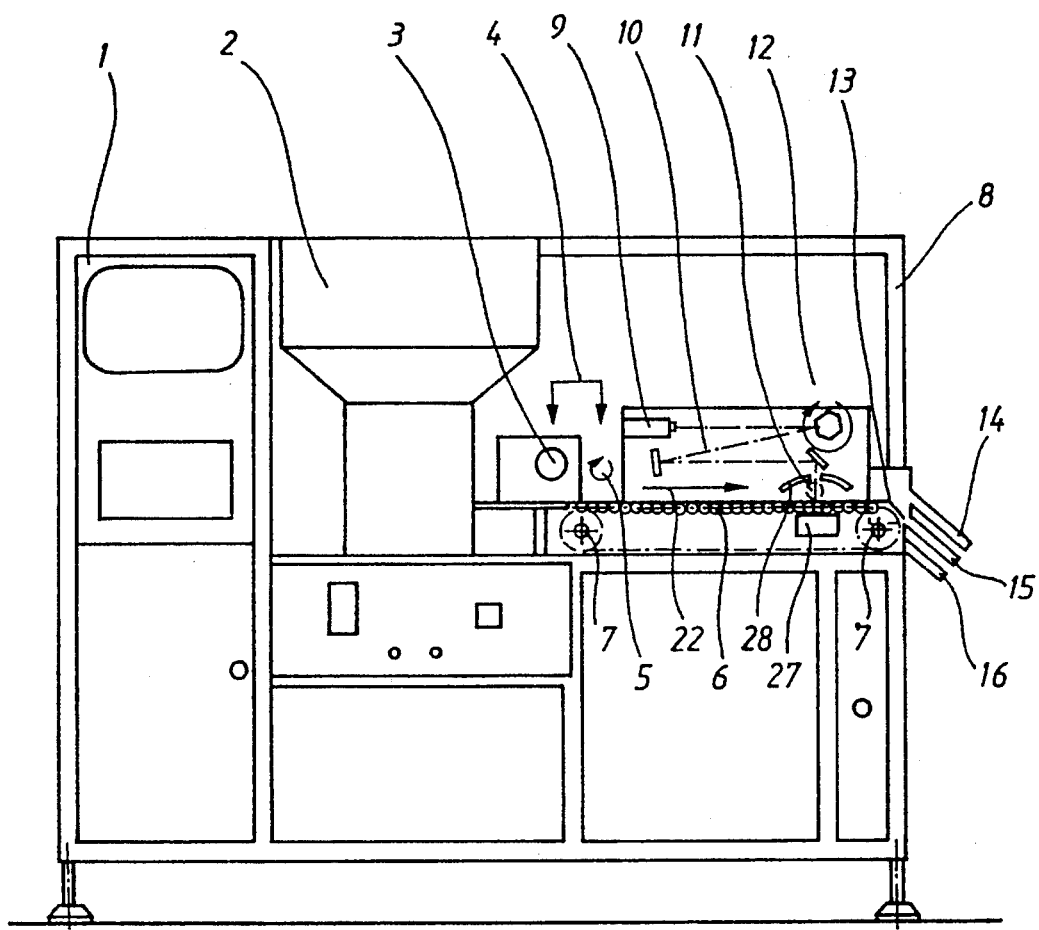
FIG. 1 is a schematic side view of the automatic sorting machine of this invention.

As per FIG. 1, the automatic sorting machine is essentially comprised of a housing 8 in which an electronic switching box is arranged which, in turn, is associated with a vibratory delivery 2. The products to be classified and to be evaluated are entered into vibration delivery 2 and are separated and isolated there. The products exit from vibratory delivery 2 in the region of an originating or starting station 3, where the products are so turned over at a turning station 4, that they are perpendicular to the conveying direction (feed direction 22) of a roller track or conveyor 6 and lie or reside on roller track 6.

In turning station 4, the products are turned 90°, namely in the direction of arrow 5.

Figure 3:
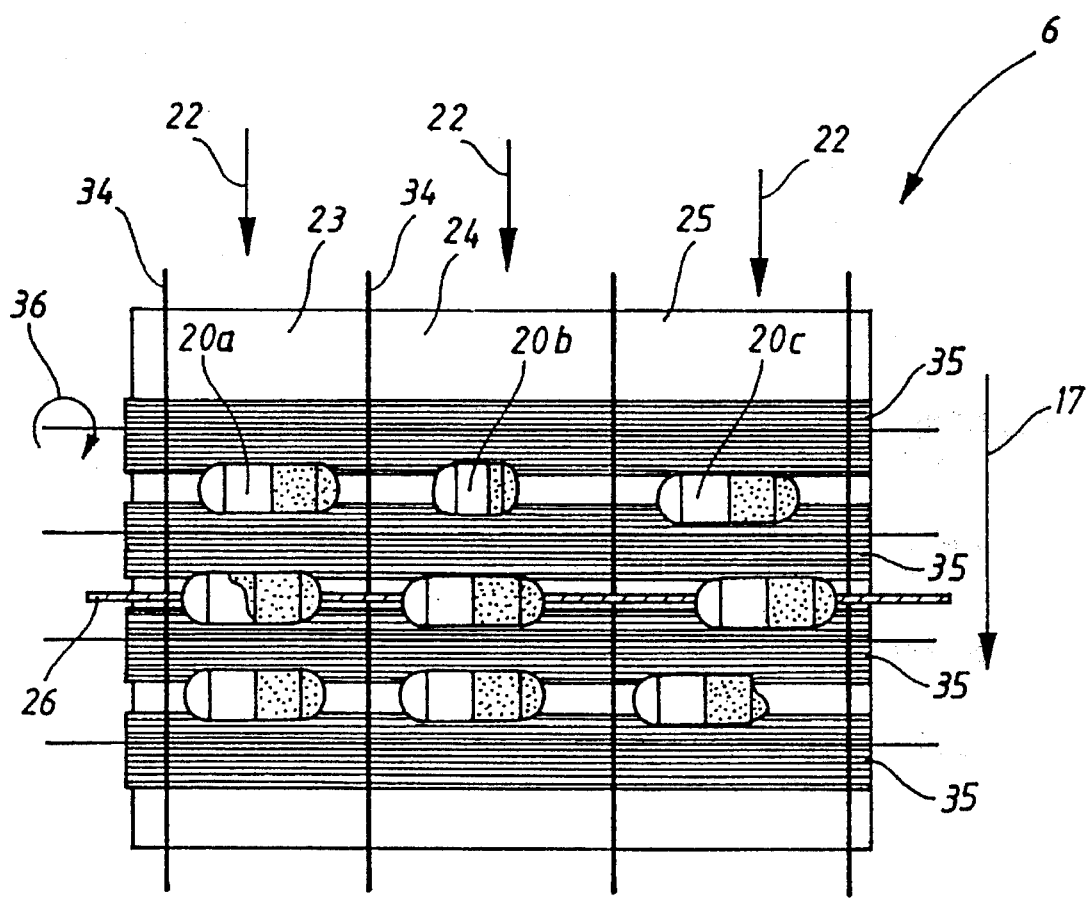
FIG. 3 is a top view looking onto the roller track.

Roller track 6 is comprised of several tracks 23, 24, 25, as seen in FIG. 3, wherein each roller 35 is additionally rotatably driven about its longitudinal axis, for example in the direction of arrow 36.

The products to be classified are loaded onto roller track 6 from turning station 4, with the roller track continuously endlessly circulating around guide roller 7.

At least one camera 9, arranged above roller track 6, has a movable beam/light path 10. Hereby, in the beam/light path of the fixed camera, lies a reorientation mirror 12, which, as will be described later, is adjustable.

In the embodiment of FIG. 1, the reorientation mirror 12 is comprised of a polygonal mirror which is turned about its longitudinal axis in the direction of the shown arrow. The beam/light path of the camera is correspondingly deflected by this polygonal mirror and impinges upon a first reorientation mirror, from which the beam/light path, via a second reorientation mirror, strikes the product to be classified, at a check point or measuring place 11.

The previously noted reorientation mirrors are not absolutely necessary. It is sufficient if a single reorientation mirror 12 is utilized, whereby the other fixed mirrors become unnecessary.

Depending upon the classification of the product, the classification signal controls an elimination station 13, which channels the product onto differing elimination tracks 14, 15, 16. For example, via upper elimination or exit track 14, the defective products are removed, while the good quality products are removed via eliminating track 15 and the unrecognized products are removed via track 16.

Figure 2:
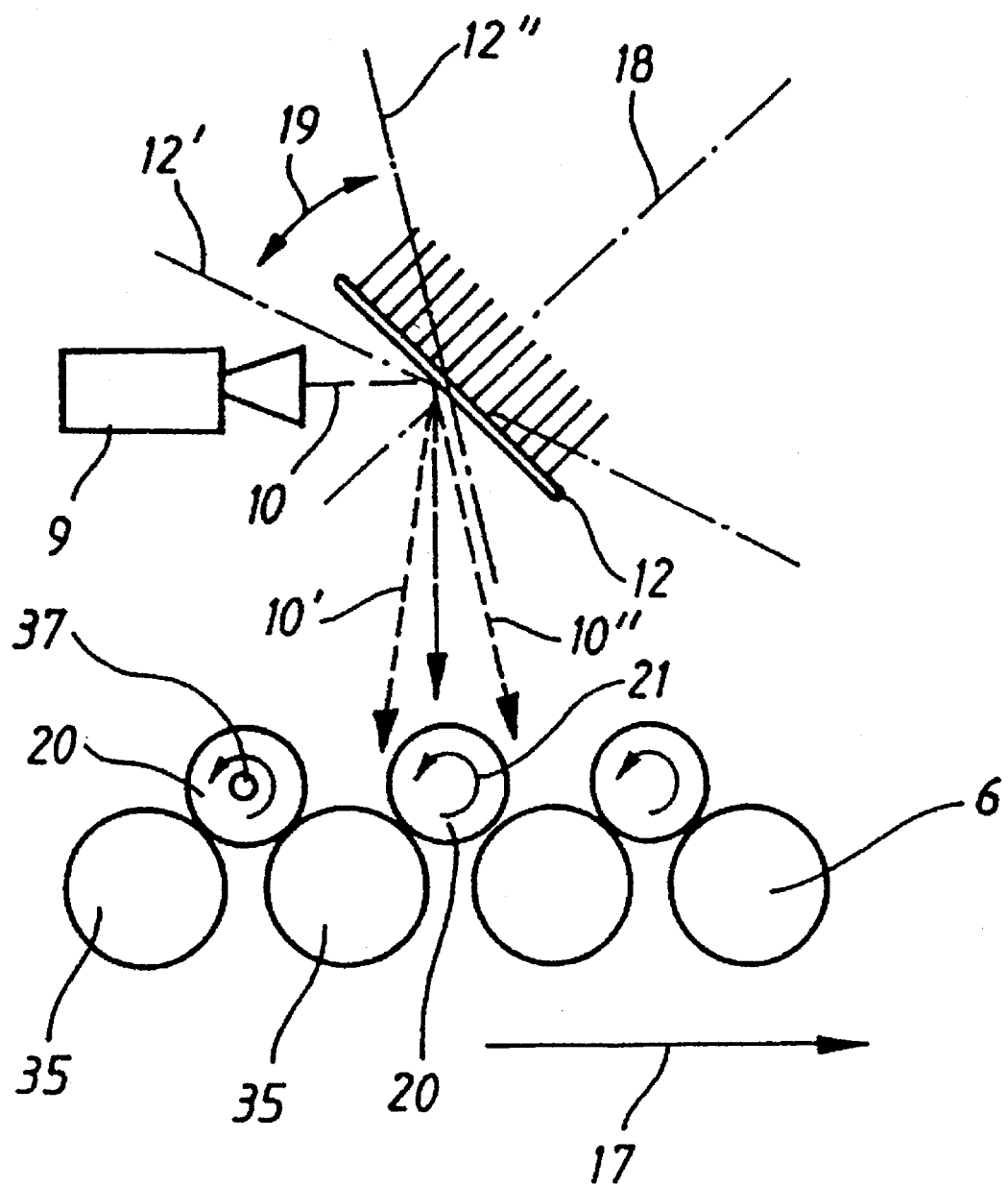
FIG. 2 is a schematic side view showing the evaluation apparatus.

The principal relationships for the determination of the product are described in more detail relative to FIG. 2. Herewith, as the embodiment for the reorientation mirror 12, a transverse mirror is utilized which can be used in place of the previously noted polygonal mirror.

This transverse mirror (reorientation mirror 12) is tilted about its center axis 18 in the direction of arrows 19, whereby it takes positions 12, 12' and 12".

Accordingly, the beam/light path 10 of camera 9 impinges upon the product at locations 10, 10', 10" and thus provides the camera with a practically fixed product since the tilting of reorientation mirror 12 is so synchronized that the beam/light path pans in the feeding direction 17 of the roller track so that the camera thus sees a fixed or non-moving product.

The beam/light path 10 of the camera thus so pans the product that the rotational axis 37 of the product and the optical axis of the camera chips coincide or unite on the line of the optical beam/light path 10, that is, that they are perpendicular to the surface of product 20.

The profile of product 20 is thus totally developed more than once, that is it is developed for about 360° and more, conditioned upon the rotational drive of the individual rollers 35, which drive product 20 in rotational direction 21 about rotational axis 37.

In place of the here-illustrated transverse mirror, the polygonal mirror previously illustrated in FIG. 1, can also be utilized as the reorientation mirror 12. Instead thereof, the camera can also be panned.

FIG. 3 shows the multi track delivery or feeding of products 20a, 20b, and 20c on each of associated tracks 23, 24 and 25 of roller track 6.

Herewith, boundary limits 34 are utilized for each of tracks 23–25, in order to assure a side guidance of product 20.

Figure 3A:
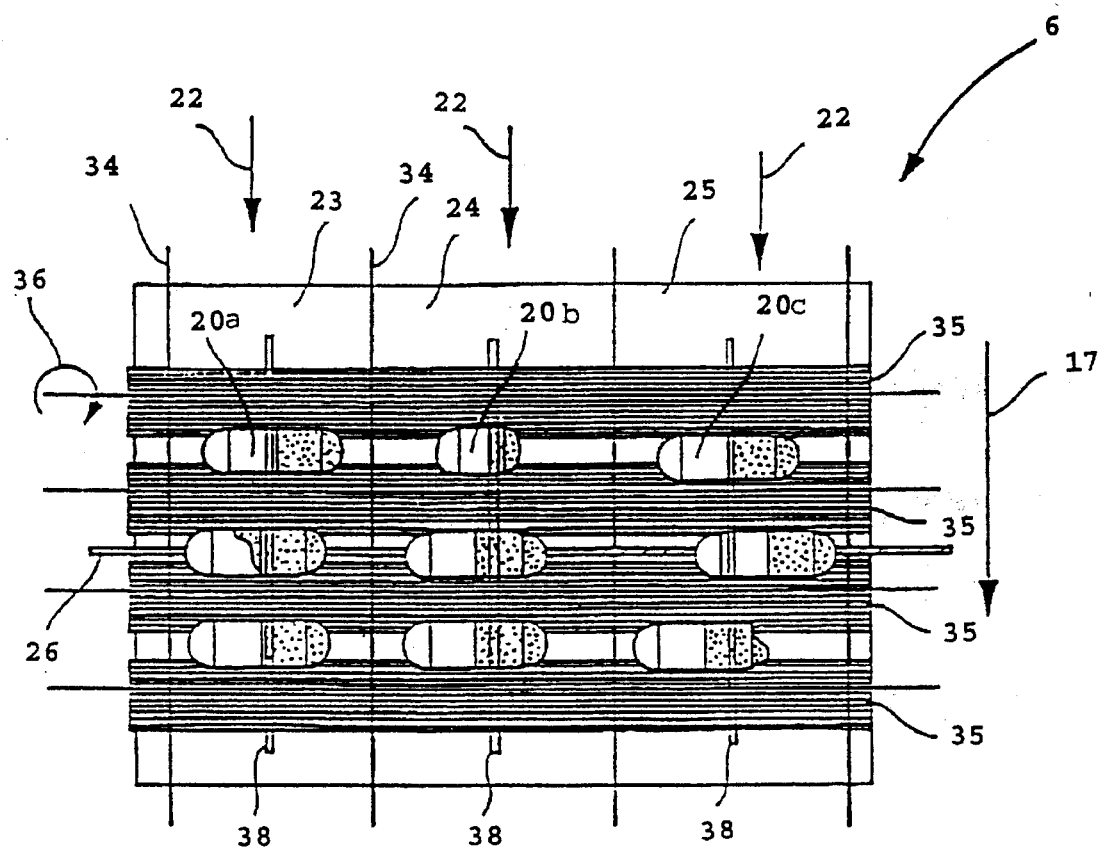
FIG. 3a is a top view, similar to that of FIG. 3, showing a modification.

In the same manner, product 20 can be protected against removal from the roller track in that above the product itself suitable strips 38, as shown in FIG. 3a, can be arranged so as to avoid a jumping out or jumping up of the product.

In a similar manner, the lateral boundaries 34 need not be attached only at tracks 23–25, which define a pocket-shaped receptacle for the product, but also extending thereabove and above the roller track 6, fixed strips can be arranged, which also assure a lateral guiding of the product.

In addition, FIG. 3 also shows that the scanning line 26 of camera 9 extends over the entire width of roller track 6, so that with a single scanning procedure, in the embodiment of this figure, at the same time, up to 10 products 20a, 20b, 20c, can be classified.

Figure 4:
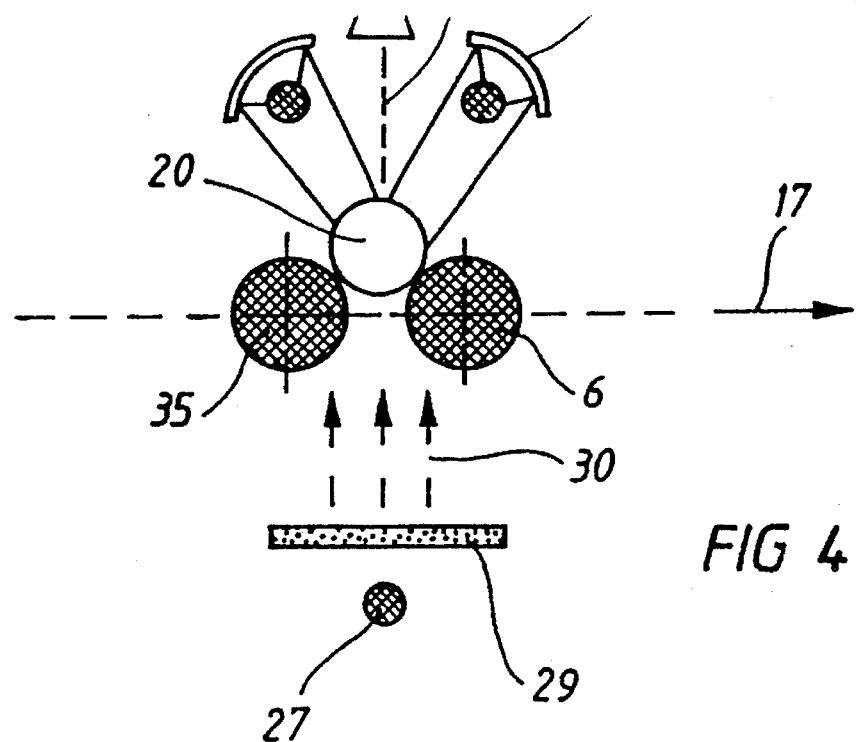
FIG. 4 illustrates the illuminating apparatus.

FIG. 4 illustrates the details of the illumination apparatus wherein, as per FIG. 1, a lower illumination device 27 is utilized, which in turn faces a replaceable color filter 29, so that the beam/light path 30 spotlights product 20 from below, between the rollers 35.

In addition, an upper illumination device 28 is utilized and has illumination bodies whose beam/light paths are reflected by associated mirrors so that a diffused white brightening light is produced on the product.

A beam/light path 10 extends above the upper illumination device 28 which, in the manner described relative to FIG. 1, is then comprehended by camera 9.

Figure 5:
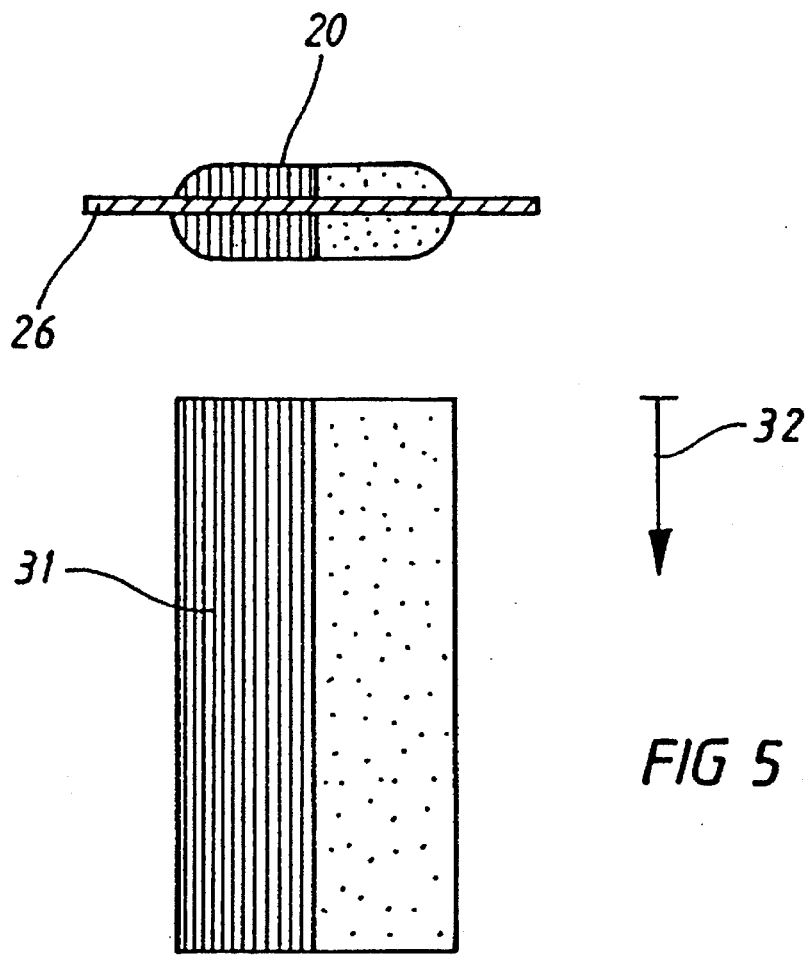
FIG. 5 illustrates the profile development or projection of the product during its conveyance through the beam/light path.

FIG. 5 illustrates a time development of the shell or surface of the product. Starting at a time axis 32, when t=0, the camera "sees" a development or unrolled shell or surface 31 of product 20, since the product turns in the scanning line and, at the same time, the beam/light path is panned in feeding direction 17.

Figure 6:
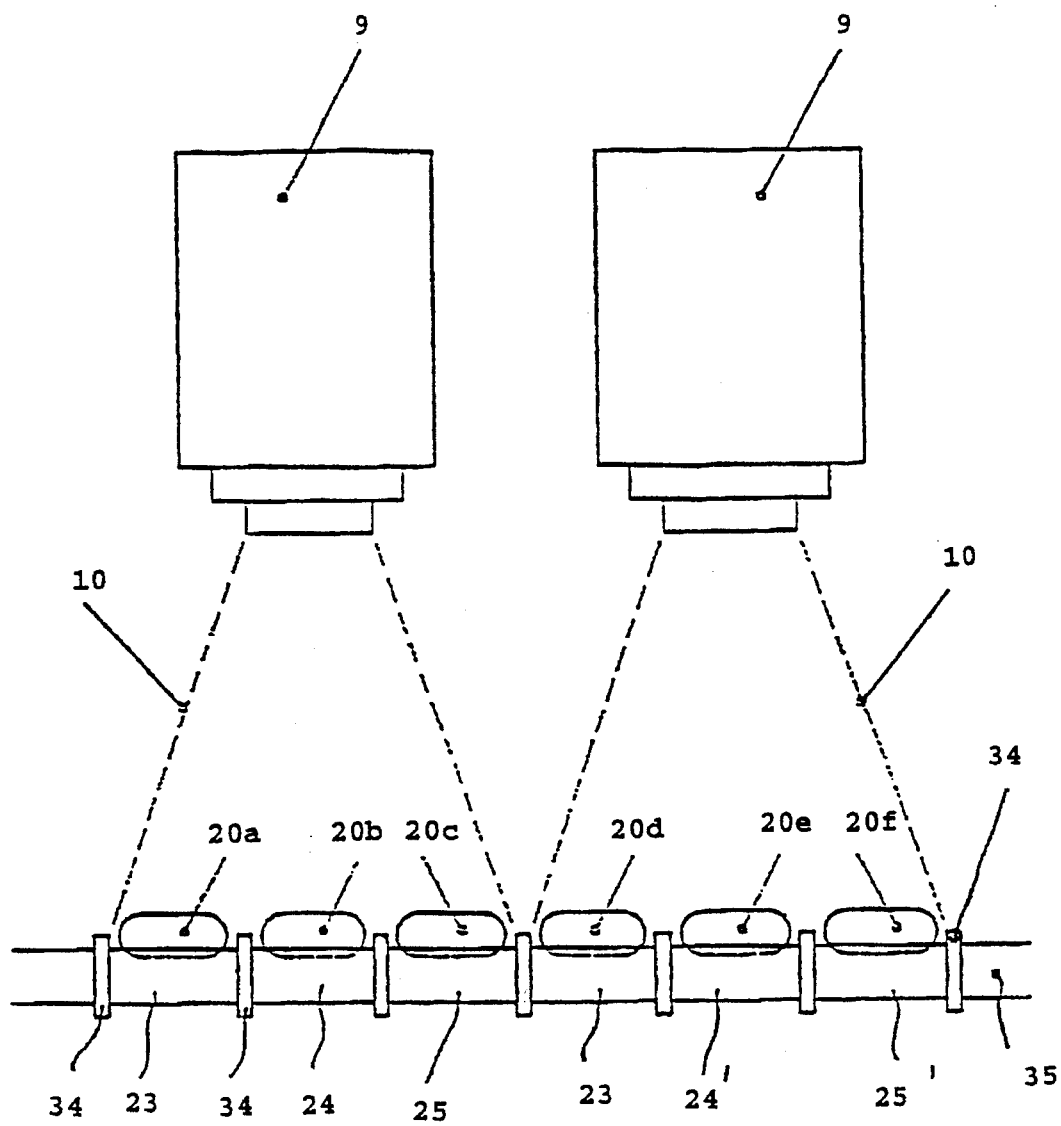
FIG. 6 is a top view, illustrating a form of the invention in which two cameras are utilized.
Figure 7:
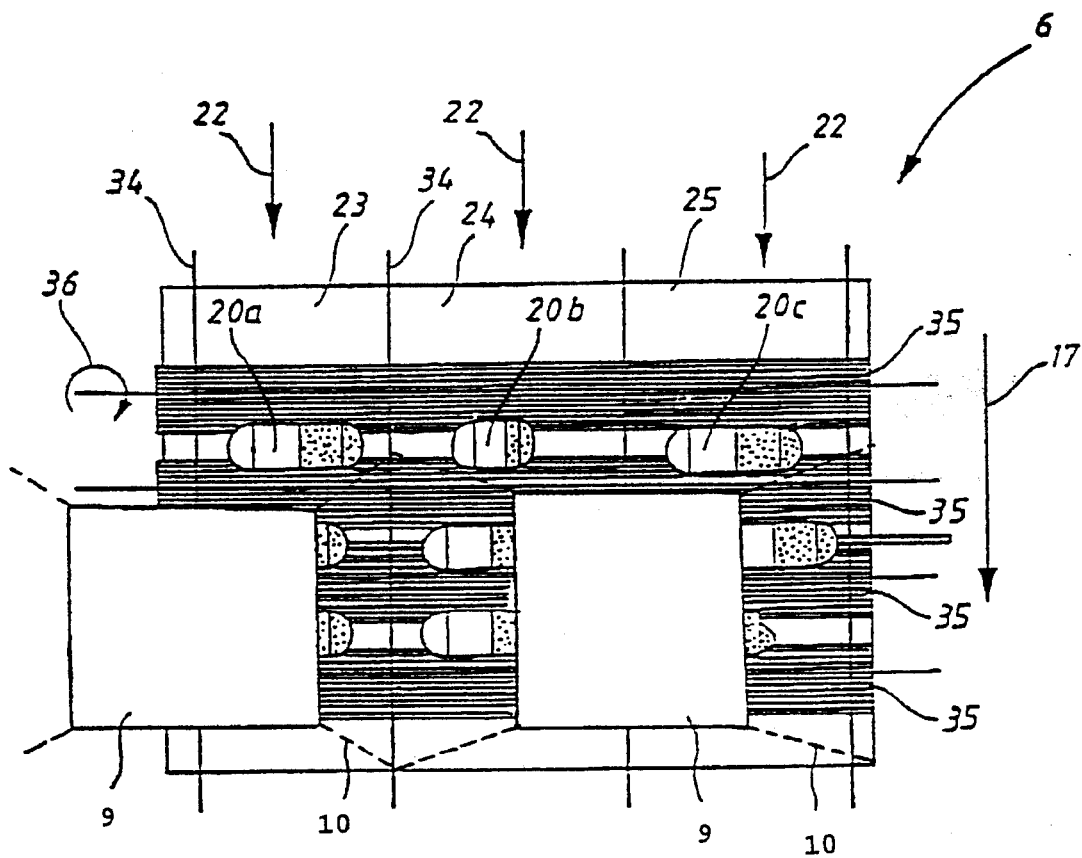
FIG. 7 is a front view of the invention shown in FIG. 6.

FIGS. 6 and 7 illustrate an embodiment in which a plurality of cameras 9 are utilized for scanning the multiple tracks of the product.

While there are shown and described present preferred embodiments of the invention, it is to be distinctly understood that the invention is not limited thereto, but may be otherwise variously embodied and practiced within the scope of the following claims and the reasonably equivalent structures thereto. Further, the invention illustratively disclosed herein may be practiced in the absence of any element which is not specifically disclosed herein.

What is claimed is:

1. An automatic sorting machine for sorting and classifying small products, by means of optoelectronic specimen recognition, the machine comprising:

a vibratory inlet device wherein the products to be sorted are separated;

a camera having a beam/light path;

a delivery device for conveying the separated products, through the beam/light path;

the camera being utilized for optically comprehending each product and for obtaining electronic signals;

means for evaluating the electronic signals for specimen recognition for deviations of the product, for producing an elimination signal, for eliminating defective products and unrecognized products, wherein the camera is a color-line camera, whose beam/light path is so movably arranged that a beam/light path thereof, in a feeding direction of the product, pans the beam/light path over a predetermined conveying track, wherein the product, during the throughput thereof through the panned beam/light path, is rotated about an axis parallel to a scanning line.

2. The automatic sorting machine of claim 1, wherein at least one of the camera and a reorientation mirror synchronously pan the feeding movement of the product.

3. The automatic sorting machine of claim 1, wherein at least one of the camera and a reorientation mirror is moved synchronously with the product over a predetermined distance.

4. The automatic sorting machine of claim 2, wherein at least one of the camera and the reorientation mirror is moved synchronously with the product over a predetermined distance.

5. The automatic sorting machine of claim 1, further including a reorientation mirror, wherein the reorientation mirror is a transverse mirror turnable about a central longitudinal axis.

6. The automatic sorting machine of claim 2, wherein the reorientation mirror is a transverse mirror turnable about a central longitudinal axis.

7. The automatic sorting machine of claim 1, further including a reorientation mirror, wherein the reorientation mirror is a polygonal mirror turnable about a longitudinal axis.

8. The automatic sorting machine of claim 2, wherein the reorientation mirror is a polygonal mirror turnable about a longitudinal axis.

9. The automatic sorting machine of claim 3, wherein the reorientation mirror is a polygonal mirror turnable about a longitudinal axis.

10. The automatic sorting machine of claim 4, wherein the reorientation mirror is a polygonal mirror turnable about a longitudinal axis.

11. The automatic sorting machine of claim 1, wherein several products are transportable parallel to each other in several adjacent paths, through the beam/light path of the camera.

12. The automatic sorting machine of claim 11, wherein several cameras are adjacently arranged, whereby each camera always surveys several paths of the products.

13. The automatic sorting machine of claim 1, wherein the delivery device is comprised of a turning station and a roller track, the roller track having rollers arranged perpendicularly to the feeding direction.

14. The automatic sorting machine of claim 13, wherein the rollers are rotatable about their respective longitudinal axes.

15. The automatic sorting machine of claim 11, wherein the delivery device is comprised of a turning station and a roller track, the roller track having rollers arranged perpendicularly to the feeding direction, the machine further including a multi track delivery of the products on correspondingly arranged tracks of the roller track.

16. The automatic sorting machine of claim 12, wherein the delivery device is comprised of a turning station and a roller track, the roller track having rollers arranged perpendicularly to the feeding direction, the machine further including a multi track delivery of the products on correspondingly arranged tracks of the roller track.

17. The automatic sorting machine of claim 15, wherein lateral boundaries are provided for each track.

18. The automatic sorting machine of claim 16, wherein lateral boundaries are provided for each track.

19. The automatic sorting machine of claim 15, wherein fixed strips are attached above the roller track.

20. The automatic sorting machine of claim 16, wherein fixed strips are attached above the roller track.

21. The automatic sorting machine of claim 1, wherein the delivery device is comprised of a turning station and a roller track, the roller track having rollers arranged perpendicularly to the feeding direction, the machine further including a lower illumination device attached underneath the roller track, the illuminating device facing a color filter in order to spotlight the product, from below, between the rollers.

22. The automatic sorting machine of claim 1, further including an attached upper illumination device, having illuminating bodies, whose beam/light paths are thusly reflected that a diffused white brightening light is produced on the products.

23. The automatic sorting machine of claim 1, wherein the products include at least one of the products of the pharmaceutical and confectionery industries.

* * * * *